United States Patent [19]

Maynarez

[11] 4,412,175
[45] Oct. 25, 1983

[54] DEBRIS ALARM
[75] Inventor: Franklin D. Maynarez, Miami, Fla.
[73] Assignee: Coulter Electronics, Inc., Hialeah, Fla.
[21] Appl. No.: 357,913
[22] Filed: Mar. 15, 1982

Related U.S. Application Data
[63] Continuation-in-part of Ser. No. 259,717, Apr. 30, 1981.
[51] Int. Cl.³ .............................................. G01N 27/00
[52] U.S. Cl. ..................................... 324/71.1; 377/12; 364/555; 324/71.4
[58] Field of Search ...................... 324/71 CP, 140 D; 235/92 PC; 340/607, 608, 609, 627; 364/555; 377/10, 11, 12

[56] References Cited
U.S. PATENT DOCUMENTS
3,444,463 5/1969 Coulter et al. ................. 324/71 CP
3,820,019 6/1974 Doty et al. ..................... 324/71 CP
3,924,180 12/1975 Salzman et al. ................ 324/71 CP

Primary Examiner—Michael J. Tokar
Assistant Examiner—Kevin O'Shea
Attorney, Agent, or Firm—Gerald R. Hibnick

[57] ABSTRACT

Disclosed is an abnormal pulse detector for use with a particle analyzing apparatus of the Coulter ® type for generating discrete particle pulses in response to liquid suspended particles passing through a sensing aperture, the abnormal pulse detector comprising: a bad pulse detector for generating a bad count pulse for each of the particle pulses which have a width that is either too long or too short, comparative pulse detector means for generating a comparative count pulse for each of the particle pulses or for each of the particle pulses not generating a bad count pulse, counter and comparator circuitry for counting the bad count pulses and the comparative count pulses and for obtaining the ratio of the bad count pulses to the comparative count pulses so as to indicate a alarm condition when the ratio reaches a predetermined, unacceptable level.

10 Claims, 7 Drawing Figures

DEBRIS ALARM

This application is a continuation-in-part of Ser. No. 259,717, Apr. 30, 1981.

BACKGROUND OF THE INVENTION

1. Field of the Invention

The present invention relates generally to particle analyzing apparatuses and more particularly is concerned with a circuit arrangement incorporated into such analyzing apparatus for detecting abnormal functioning of the particle sensing function of the analyzing apparatus caused by some obstruction thereof.

2. Description of the Prior Art

In U.S. Pat. No. 3,259,891 to Coulter et al. there is disclosed a debris alarm for a particle analyzing apparatus, wherein the particle pulses are monitored by a higher than normal threshold. The portions of the pulses above this threshold are converted to constant amplitude pulses, which are integrated to obtain their widths. If a given pulse width exceeds some predetermined width, an alarm condition is triggered.

In particle sensing undertaken in the above described particle analyzer, which is sold under the trademark Coulter Counter ®, there are several possible situations where debris in the liquid sample suspension being processed can affect the particle count. First, debris that passes through the sensing aperture generally results in a long pulse, which is usually a result of the debris being long in length and/or proceeding through the aperture at a rate slower than smaller particles. This condition results in the loss of counts for particles during the time period in which the debris is passing through the orifice. Secondly, the debris can partially block the sensing aperture, resulting in particle pulses that have abnormally short widths and abnormally high amplitudes. Such a condition results in bad mean cell volume measurements, due to the debris caused reduction of the aperture's diameter and off axis longer trajectories of the particles through the aperture path. Moreover, in systems having positive displacement fluid movement through the aperture, a partial blockage will increase the velocity of the sample flow through the aperture, thereby narrowing the width and increasing the amplitude of the particle pulses. As a result, particle pulses can be generated that are too narrow for a proper response by an amplifier in the detection circuitry of the particle analyzer. Additionally, various sources of electronic noise can create narrow pulses that can be confused as particle pulses.

In view of the possible debris condition described above, it can be seen that U.S. Pat. No. 3,259,891 is only able to detect abnormally long pulses on a pulse-by-pulse basis. Hence, this design is deficient in the following ways: This design is not able to detect pulses that are abnormally short, such as those caused by electronic noise or by a partially blocked aperture. Secondly, the design of the prior art requires that the pulse exceed a relatively high threshold level, meaning that some debris may generate particle pulses, yet not exceed this threshold. Thirdly, the technique only examines pulses on an individual basis, and does not provide a benchmark or reference point for determining how much debris exists in the processed sample. In other words, a single piece of debris might trigger the alarm, and it might be the only piece of debris in the sample.

Accordingly, it can be seen that there is a need in the particle analyzer art to have a debris alarm which can detect pulses which are both too short and too long and, after such detection, determine how many such bad pulses there are with respect to some benchmark or reference number.

SUMMARY OF THE INVENTION

The invention provides an abnormal pulse detector for an electronic particle analyzing apparatus, wherein a particulate suspension and an electric current are simultaneously passed through a particle sensing aperture so as to generate discrete particle pulses. The abnormal pulse detector comprises: bad pulse detector means, for generating a bad count pulse for each of the particle pulses which has a width that is either too long or too short; comparative pulse detector means, for generating a comparative count pulse for each of the particle pulses or for each of the particle pulses not generating a bad count pulse; counter and comparator means, for counting the bad count pulses and the comparative count pulses and for comparing the number of the bad count pulses to the number of the comparative count pulses; and debris indicator means, for indicating when the number of the bad count pulses, when compared to the number of the comparative count pulses, reaches a predetermined level.

In addition to the use of the bad pulse detector means in combination with the comparative pulse detector means, the bad pulse detector means can provide a bad count pulse for numerous applications. The bad pulse detector means comprises threshold means for generating a threshold pulse for each particle pulse which exceeds a predetermined threshold level and means for generating a time window wherein threshold pulses that end outside of the time window are counted as bad pulses.

BRIEF DESCRIPTION OF THE DRAWINGS

Further objects and advantages of the present invention will become apparent as the following description proceeds, taken in conjunction with the accompanying drawing in which:

FIG. 3 is a more detailed block diagram of one embodiment of the system illustrated in FIG. 2;

DETAILED DESCRIPTION OF THE EMBODIMENT

Figure 1:
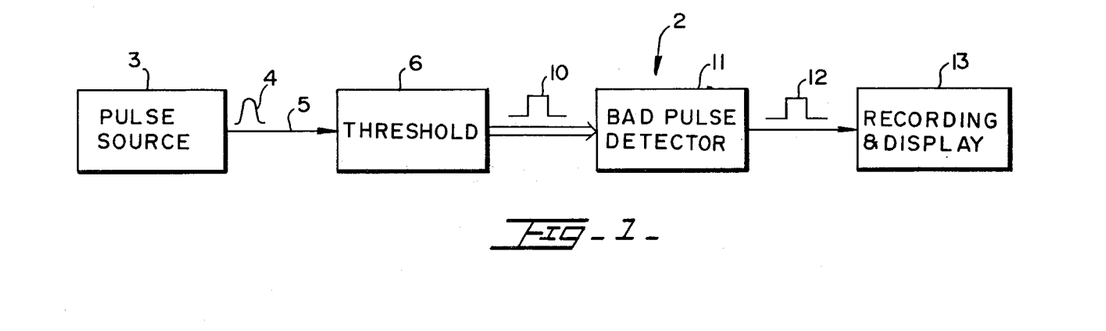
FIG. 1 shows a block diagram of the abnormal pulse detector improvement of this invention.

Referring to FIG. 1, there is shown an abnormal pulse detector embodying the invention and identified generally by the referenced number 2. A pulse source 3 comprises a particle sensing aperture and related circuitry of a particle detector, such as shown and described in U.S. Pat. Nos. 2,656,508 and 3,259,842, wherein particle pulses 4 are developed in response to the passage of particles in a particulate suspension through the sensing zone of the particle sensing aperture. More specifically, an electric current passes through the particle sensing aperture and particle pulses are produced as a result of the modulation of this current by the passage of particles through the particle sensing aperture. Each pulse amplitude is approximately proportional to the size or volume of the pulse producing particle. Although the abnormal pulse detector 2 embodying the present invention is utilizable with all types of Coulter Counter ® apparatuses, it is particularly useful with those designs having a constant volume displacement per unit time pump to draw the sample suspension containing particles through the particle sensing aperture, as shown in U.S. Pat. No. 4,001,678.

The particle pulses 4, developed by the pulse source 3, are coupled via a conductor 5 to a threshold circuit 6. Threshold pulses 10 of a fixed amplitude are fed from the threshold circuit 6 to a bad pulse detector 11, which includes pulse width discriminating circuitry, which generates a bad count pulse 12 when abnormally long or short pulses occur due to factors, such as a blockage of the sensing aperture. More specifically, upon setting a range of acceptable pulse widths, the bad pulse detector 11 sets a time window. If a given pulse 10 is too short or too long in duration, i.e., width, then it falls outside of the window and the detector 11 generates the bad count pulse 12 indicating that the received threshold pulse 10 and therefor the originating particle pulse 4 is a bad pulse. The specific components of the bad pulse detector will be discussed in detail hereinafter.

The bad pulse information generated by the bad pulse detector 11 can be used in numerous ways, as will be apparent to those skilled in the art. One very simple usage would be to merely use a data recording and display means 13, which would allow the display of the total number of bad count pulses. Typically, the recording and display means 13 would include an integrator for accumulating the bad count pulses. This recorded data can be coupled to a means for triggering a debris alarm, should the total value or number of bad count pulses reach a predetermined number during an operational count cycle of the pulse source 3 or after some predetermined time period of operation. Alternatively, the summation of the time of the bad count pulses can be compared to the total operational time and, if high enough, can trigger an alarm condition.

Figure 2:
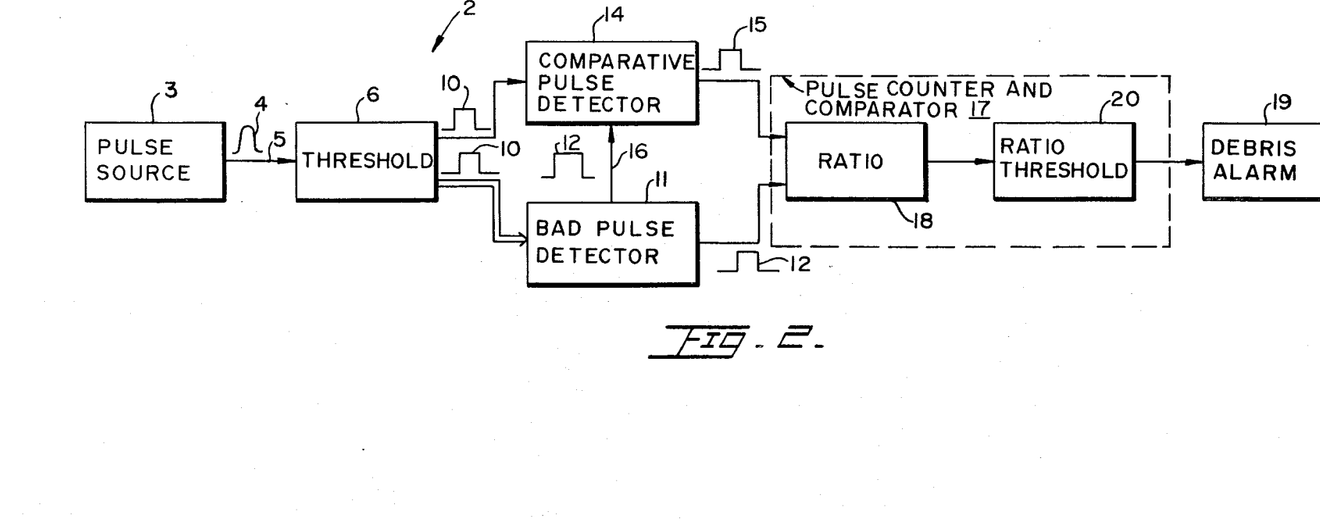
FIG. 2 shows a bad pulse detector implemented in an abnormal pulse detector, wherein bad count pulses generated from the bad pulse detector are compared to a reference.

FIG. 2 illustrates one implementation of the bad pulse detector 11 which has proven to be extremely useful, in that the bad count pulses are not only counted, but they are compared to the total count pulses or alternatively, the good count pulses. Good count pulses are equal in number to those threshold pulses 10 that do fall into the heretofore described window, while total count pulses are equal in number to the sum of good and bad count pulses 12. This comparison of bad count pulses with "comparative" count pulses, i.e., total count pulses or good count pulses, allows for a benchmark or reference point for the bad count pulses, so that the number of bad count pulses can be correlated with the amount of debris in the liquid sample being processed through the sensing aperture. More specifically, in FIG. 2, the threshold pulses 10 are fed to not only the bad pulse detector 11, but also to a comparative pulse detector 14; which, in the embodiment of FIG. 2, generates an output pulse, i.e., a comparative count pulse 15, for each threshold pulse 10. Alternatively, the bad pulse detector 11 could be used to gate the comparative pulse detector 14, by feeding the bad count pulses 12 to the detector 14 via a conductor 16. The concurrence of pulses 10 and 12 in the detector 14 inhibits its output, so that detector 14 generate the pulse 15, i.e., a good count pulse, only when there was a good threshold pulse 10. In summary, the detector 14 can generate a signal representing total count pulses or good count pulses, i.e., comparative count pulses 15.

In a pulse counter and comparator means 17, the hereinafter described comparisons of data for the comparative and bad count pulses can be made by a ratio means 18 to give a ratio. Moreover, when this ratio exceeds a predetermined value, defined as R, a debris alarm 19 in the form of, for example, a noise or light emitting device can be activated by ratio threshold means 20. The alarm conditions are indicated mathematically as follows:

$$\frac{\text{Bad Pulses}}{\text{Total Pulses}} \geq R_{B/T}$$

$$\frac{\text{Bad Pulses}}{\text{Good Pulses}} \geq R_{B/G}$$

Figures 4, 5:
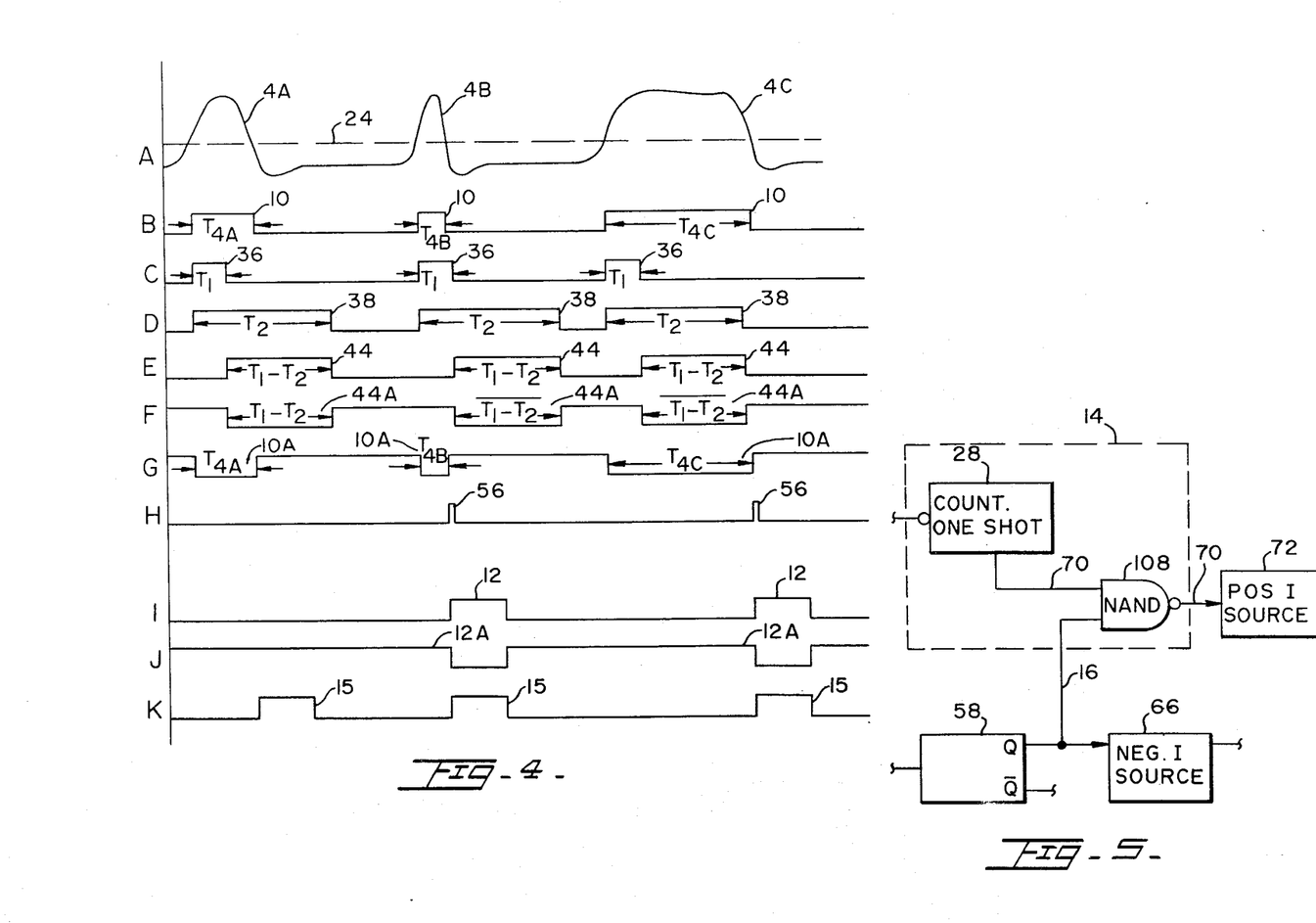
FIG. 4 shows the graphs of the electrical signals at various points of the embodiment illustrated in FIG. 3.
FIG. 5 shows an alternative modification to the system shown in FIG. 3.

FIG. 3 illustrates the specific circuitry design of the bad pulse detector 11 and the specific circuitry for one embodiment of the generalized diagram of FIG. 2. Graph A in FIG. 4 shows the waveforms of illustrative particle pulses 4 as they appear at the conductor 5 of FIG. 3, with the individual pulses being identified by the reference numbers 4A, 4B, and 4C. The threshold circuit 6 has a low threshold level. This low threshold level is represented by a dashed line 24 in Graph A of FIG. 4. When the low threshold level 24 is exceeded by a particle pulse 4, the threshold circuit 6 develops the threshold pulse 10 having a fixed amplitude and duration which is equal to the period that the particular particle pulse exceeds the threshold level. Graph B of FIG. 4 shows the threshold pulses 10, which are square waveforms, developed in response to the particle pulses 4A, 4B, and 4C. The pulse duration of the pulses are $T_{4A}$, $T_{4B}$, and $T_{4C}$, respectively. The threshold pulses 10 shown in Graph B are developed as an output of threshold circuit 6 at a conductor 26.

As shown in FIG. 3, the output of the threshold circuit 6 on the conductor 26 is coupled to the inputs of three one shots 28, 30 and 32. The one shots 30 and 32 comprise a part of the bad pulse detector 11, which generates an output when abnormally long or short particle pulses occur, for example due to blockage of the sensing aperture by debris. More specifically, the rising edge of each threshold pulse 10 is used to trigger the one shots 30 and 32. Upon being triggered, the one shot 30 provides minimum width pulses 36 having pulse durations $T_1$, as shown in Graph C of FIG. 4. The pulse duration $T_1$ is set so as to represent the minimum acceptable width for the threshold pulses 10. Likewise, upon being triggered, the one shot 32 produces a maximum width pulse 38 having a pulse duration of $T_2$, as shown in Graph D of FIG. 4. The minimum and maximum width pulses 36 and 38 are applied to a pair of conductors 40 and 42, respectively, and are fed to a XOR (EXCLUSIVE OR) gate 43. The XOR gate 43 obtains the difference between the two pulses 36 and 38 and has as an output a difference pulse 44 having a pulse duration of $T_1-T_2$, as shown in Graph E of FIG. 4.

The threshold pulses 10, in addition to being fed to the three one shots, are also fed to an inverter 48, so as to obtain inverted threshold pulses 10A as shown in Graph G of FIG. 4. These inverted threshold pulses 10A are applied to a conductor 50 and are fed to a clock input of a D-type flip-flop 52. The difference pulses 44, provided as an output from the XOR gate 43, are inverted by an inverter 54 to produce inverted difference pulses 44A, as illustrated in Graph F of FIG. 4. These pulses 44A are fed to the data input D of the flip-flop 52. The flip-flop 52 will toggle on the rising edge of each pulse 10A, only if the data input is a logic one. In other words, as long as the flip-flop 52 is receiving the inverted difference pulses 44A, it cannot produce an output pulse at its output Q. This condition is illustrated in Graph H of FIG. 4 for the pulse 4A, which falls within the acceptable pulse width; therefore, it does not generate a signal from the flip-flop 52. On the other hand, if the rising edge of the inverted threshold pulse 10A is received by the clock input while the inverted difference pulse 44A is not being fed to the data input, then a flip-flop output signal 56 is generated, as illustrated in Graph H of FIG. 4. In FIG. 4 the particle pulses 4B and 4C represent situations wherein the particle pulses are too short and too long, respectively; hence, each of the pulses 4B and 4C generate the flip-flop output signal 56.

The signal 56 from the flip-flop 52 triggers a one shot 58 to generate two output signals at a Q output and a Q NOT output, as shown in FIG. 3. As shown in Graph J of FIG. 4, a reset signal 12A is developed at a conductor 62 and is fed to the clear input of the flip-flop 52 to reset the Q output of the flip-flop to zero. This results in the signal 56 having a pulse width which is basically a function of the delay time of the one shot 58. The Q output of the one shot 58 provides the bad count pulse 12, as shown in Graph I, to a negative current source 66 to gate the same on.

As previously mentioned, the threshold pulses 10 are coupled to the input of the one shot 28, which provides a total count pulse 15, as shown in Graph K of FIG. 4, having the same duration as the bad count pulses 12. The total count pulses 15 are provided on a conductor 70 and are coupled to the input of a positive current source 72. The outputs of the positive and negative current sources 72 and 66 and coupled by way of diodes 74 and 76, respectively, to a common connection point 78. The values of the currents for the positive and negative current sources 72 and 66 are set at some desired ratio. When a MOS FET switch 80 is "on", an analog inverting integrator 82 sums the two currents from the two sources 72 and 66, so as to provide an analog representation of the ratio of bad count pulses to total count pulses, as will be explained in more detail hereinafter. The switch 80 is gated to its "on" state by manually or automatically applying to a conductor 85 an enable count pulse 84, provided by a manually operated push button or exterior control circuitry (not illustrated), to the input of a MOS FET driver 86, which in turn provides a sufficiently large signal 87 by way of a conductor 88 to activate the switch 80 to its "on" state. The output of the integrator 82 is coupled to the input of a comparator 90 by way of a conductor 92. The other input of the comparator 90 is coupled through a positive biasing voltage source 94 to ground. The output of the comparator 90 is coupled to one of the inputs of an AND gate 96, so as to provide thereto a debris or alarm signal 97. The enable count pulse 84 is also coupled through an inverter 98 to the other input of the AND gate 96, so as to provide thereto an inverted enable count pulse 84A, which when present holds the gate 96 disabled. The output signal of the AND gate 96 activates the debris alarm 19.

Initially the output of the integrator 82 at the conductor 92 is at 0 volts. This causes the output of the voltage comparator 90 to be zero. When the count cycle is initiated by the enable count pulse 84, the switch 80 is turned on, causing the integrator 82 to start charging. As an illustrative example, assume that the negative and positive current sources 66 and 72 are set so that their absolute current values have a ratio of 20 to 1. Also, assume that the voltage of the biasing source 94 is set to 0 volts. As the integrator 82 receives pulses from the positive current source 72, the integrator will start charging in a negative direction; thereby keeping the output of the comparator at zero. When bad pulses are generated by the negative current source 66, the integrator 82 starts charging toward the positive direction. With the above stated current ratio, as soon as the number of bad count pulses exceeds 5% of the total number of count pulses, the integrator 82 provides an output which will go positive. This positive output causes the output of the comparator 90 to go from a logic zero to a logic one, i.e., an alarm signal 97. If the comparator 90 is generating the alarm signal 97 at the end of the count period, which means that at that time at least 5% of the particle pulses were bad, then the end of the count enable pulse 84 will cause the inverted pulse 84A to cease and enable the gate 96 to pass the alarm signal 97 to the alarm unit 19. A reset pulse 104 is generated at the beginning of each operational count cycle by a manual push button or by exterior circuitry. The reset pulse 104 is provided to a MOS FET driver 105, which in turn provides a modified reset pulse 106 to reset the integrator 82.

In some applications of the particle analyzing device, when only several hundred counts occur during the count cycle, a small number of bad pulses might activate the alarm 19. To prevent this, a small positive bias voltage can be applied by the voltage source 94, such bias voltage allowing for the count of several thousand of total pulses prior to activating tha alarm 19.

A slight modification to the abnormal pulse detector 2 is illustrated in FIG. 5 wherein a NAND gate 108 is interposed into the conductor 70, with one input of the NAND gate receiving the total count pulses from the one shot 28 and the other input of the NAND gate receiving bad count pulses from the Q output of the flip-flop 58 via the conductor 16 which was first discussed with reference to FIG. 2. Hence, the count pulse from the one shot 28 is gated out when there is a bad count pulse, resulting in the NAND gate 108 providing only good count pulses to the ratio means 18 so as to allow for the calculation of the ratio of bad count pulses to good count pulses. Those skilled in the art will realize that the bad count pulses can be subtracted from the total count pulses to give good count pulses at other locations in the circuitry, such as in the pulse counter and comparator means 17.

Although the already discussed embodiments work quite well when the particles are of the same general size and thus their pulses 4A are of the same general amplitude, a problem can arise if some of the particles, not debris, are of significantly smaller size. Such circumstance will arise, for example, in the analysis of blood cells, with platelets in a whole blood sample being much smaller than the red and white cells being counted. Being much smaller, those particles would generate pulses more like 4B than 4A, i.e., of lower amplitude and shorter duration. It is not desirable to identify them as bad pulses. The FIG. 6 embodiment discriminates with respect to pulse duration and amplitude, so that only pulses above a size threshold and also too narrow or too wide will be considered as bad pulses.

Figure 6:
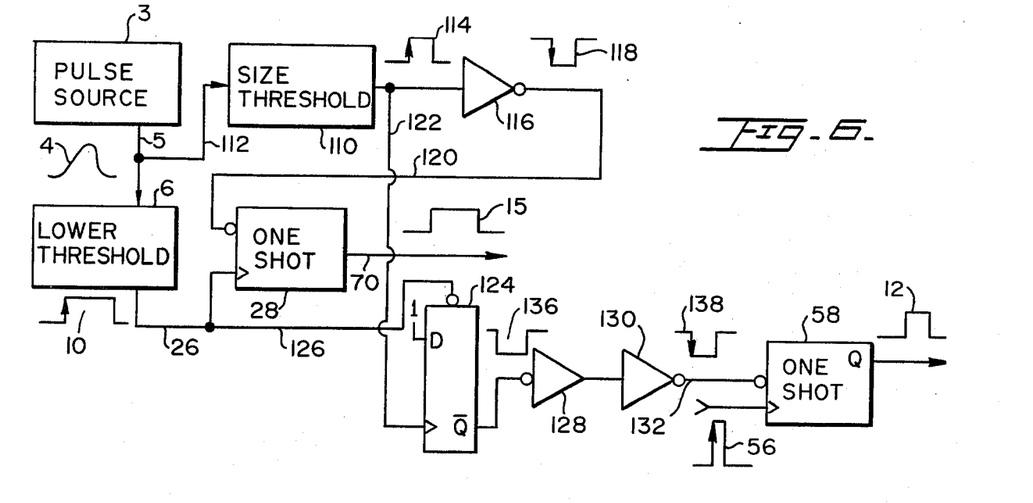
FIG. 6 shows a modified embodiment of the system of FIG. 3.

The embodiment represented by FIG. 6 is the same as that described with respect to FIG. 3, except for the following discussed additions and changes to the circuitry. However, for simplicity of illustration, only a portion of the FIG. 3 structure is shown. An upper or size threshold circuit 110 is coupled by a conductor 112 to the conductor 5, so as to receive the particle pulses 4. When the particle pulse exceeds the size threshold level of the upper threshold 110, a square wave pulse 114 is generated and then is inverted by an invertor 116 to create an inverted pulse 118 that is fed by an electrical conductor 120 to the trailing edge trigger input of the one shot 28. The pulse 114 is fed by a conductor 122 to a D-type flip-flop 124. The enable input terminal of the flip-flop 124 is coupled to the conductor 26 by a conductor 126, so as to receive the lower threshold pulses 10. The conductor 26 is coupled to the leading edge trigger input of the one shot 28. The Q NOT output terminal of the flip-flop 124 is coupled through a pair of invertors 128 and 130 by a conductor 132 to the trailing edge trigger input terminal of the one shot 58.

Figure 7:
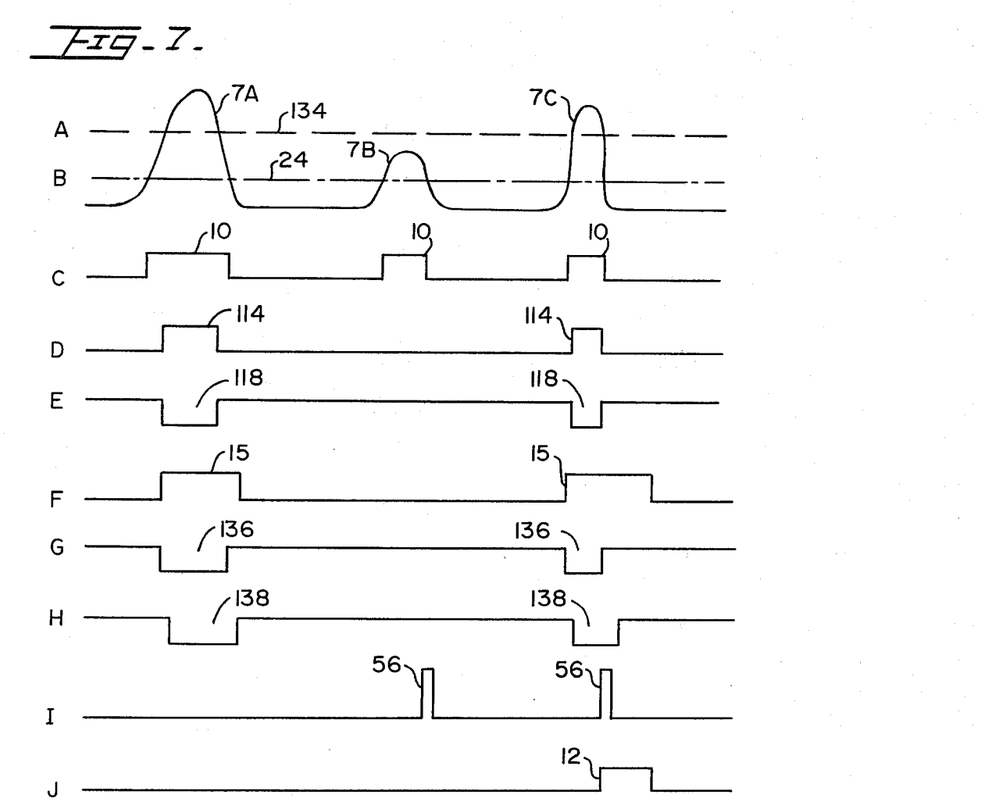
FIG. 7 shows graphs of electrical signals pertinent to the FIG. 6 embodiment.

The operation of the improvement incorporated into the embodiment of FIG. 6 can be illustrated by examining the various wave forms of the electrical signals at various points in the circuitry of FIG. 6 and as shown in FIG. 7. To illustrate the operation of the invetion, three sample pulses are shown in Graph A of FIG. 7 and are specifically identified as pulse 7A, 7B and 7C. In the same manner as accomplished with the embodiment of FIG. 3, the three illustrated particle pulses 7A, 7B and 7C generate low threshold pulses 10, using the threshold level 24, as illustrated in Graph C. Additionally, particle pulses 7A and 7C exceed the upper threshold level 134 of the threshold means 110, so as to generate the upper threshold pulses 114 as shown in Graph D. However, the pulse 7B, for example the pulse caused by a platelet, has an insufficient amplitude to cause an upper threshold pulse 114. As can be seen in Graph C, both of the pulses 7B and 7C generate narrow pulses 12. For the purposes of explanation, the width of the pulse 7A is assumed to be within the normal range of the window of the bad pulse detector 11, and both of the pulses 7B and 7C have abnormally narrow widths.

In the embodiment of FIG. 3, the widths of the pulses 7B and 7C would be such that a bad count pulse 12 would be generated for each of these pulses; whereas, the width of the pulse 7A is such that a bad count pulse 12 would not be generated. However, the FIG. 6 modification of this embodiment will prevent a bad count pulse 12 and a comparative pulse signal 15 from being generated by the platelet-caused pulse 7B. In short, when particle pulses fail to exceed the upper or size threshold 134, the development of a bad count pulse 12 and a comparative pulse signal 15 is inhibited, as next will be described.

The one shot 28 will be triggered to generate the comparative pulse signal 15 only when its leading edge trigger terminal, which is coupled to the low threshold pulses, is high and its trailing edge trigger terminal goes low, which is coupled to the inverted high threshold signal 118. As shown in Graphs D and E, when a size threshold pulse 114 is generated, its inverted pulse 118 will trigger the one shot, since the leading edge trigger terminal of the one shot already was made high by the lower threshold pulse 10. The triggering of the one shot 28 generates the comparative pulse signal 15, shown in Graph F.

The upper threshold pulse 114 is fed to the flip-flop 124 and triggers the pulses 136 from the Q NOT output, as shown in Graph G. The pulses 136 are passed through the two invertors 128 and 130 to create a delayed pulse 138, which is shown in Graph H. When the delayed pulse 138 is received by the one shot 58, it is enabled, so that by receiving the leading edge of the pulse 56 (Graph I) from the flip-flop 52, the one shot 58 is triggered to generate a bad count pulse 12 for the particle pulse 7C, but not for the particle pulse 7A, as shown in Graph J. The particle pulse 7A does not generate a bad count pulse 12, because a pulse 56 is not generated by the window of the bad pulse detector. The flip-flop 124 is cleared by the threshold pulse 10 at its clear terminal.

As illustrative values, the one shots 30 and 32 can be set at 10 microseconds and 40 microseconds, respectively, to give a time window for acceptable pulses which extends from 10 to 40 microseconds. The one shots 28 and 58 can, for example, be set at 15 microseconds.

Although particular embodiments of the invention have been shown and described herein, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What we claim is:

1. An abnormal pulse detector for use with a particle analyzing apparatus for studying particles in suspension, said apparatus including a particle sensing aperture through which said particles in suspension are passed, means for passing an electric current through said aperture simultaneously with passage of a particle through said aperture, and detecting means responsive to impedance variations for generating a discrete particle pulse with the passage of said particle through said aperture, said abnormal pulse detector comprising: bad pulse detector means for generating a bad pulse signal for each said particle pulse which has an abnormal width; accumulating means for accumulating said bad pulse signals; comparator means for comparing the accumulated bad pulse signals to a predetermined standard representative of an undesirable level of said bad pulse signals; alarm indicator means for indicating that the accumulated bad pulse signals have reached said undesirable level.

2. The abnormal pulse detector according to claim 1, which further includes comparative pulse detector means for generating a comparative pulse signal for one of each said particle pulse, and each said particle pulse not generating a bad pulse signal; said accumulating means is operative for accumulating said comparative pulse signals and for comparing the accumulated bad pulse signals to the accumulated comparative pulse signals; said predetermined standard being a function of the number of said bad pulse signals relative to the number of said comparative pulse signals.

3. The abnormal pulse detector according to claim 1, wherein said bad pulse detector means is operable to generate a bad pulse signal for each said particle pulse when said abnormal with is either too long or too short.

4. The abnormal pulse detector according to claim 1 or 2, wherein said comparator means includes ratio means for calculating the ratio of bad pulse signals to comparative pulse signals and further includes ratio threshold means for determining when said ratio reaches a predetermined level representative of said undesirable level of said bad pulse signals.

5. The abnormal pulse detector according to claim 4, in which said ratio means includes current sources of opposite polarity, each coupled respectively to receive said comparative pulse signals or said bad pulse signals; and said ratio threshold means includes means for accumulating current from said current sources in proportion to the number of said comparative pulse signals and said bad pulse signals; whereby, when the accumulation at a predetermined time is of a polarity representative of the polarity of said bad pulse signals, said alarm indicator means is triggered.

6. The abnormal pulse detector according to any one of claims 1, 2 or 3, wherein said bad pulse detector means includes particle pulse threshold means for generating a threshold pulse for each particle pulse which exceeds a predetermined threshold level, said threshold pulse has a duration which is a function of the width of said particle pulse at said predetermined threshold level, and said threshold pulse is applied to said bad pulse detector as representing the particle pulse.

7. The abnormal pulse detector according to claim 6, wherein said bad pulse detector means includes: means for creating a time window beginning at a first predetermined time and ending at a second predetermined time, means for determining if the end of each said threshold pulse falls outside of said time window, and means for generating said bad pulse signal when said threshold pulse ends outside of said window.

8. The abnormal pulse detector according to claim 6, wherein said bad pulse detector means includes: means for generating a minimum width pulse of a first predetermined duration in response to the beginning of each said threshold pulse, said minimum width pulse representing the minimum acceptable duration of each said threshold pulse; means for generating a maximum width pulse of a second predetermined duration in response to the beginning of each said threshold pulse, said maximum pulse representing the maximum acceptable duration of each said threshold pulse; means for correlating said minimum width pulse and said maximum width pulse to generate a time beginning at the end of said minimum width pulse and ending at the end of said maximum width pulse; means for determining if the end of each said threshold pulse does not occur during said time window; and means for generating said bad pulse signal for each said threshold pulse which does not end during said time window.

9. The abnormal pulse detector according to claim 8, wherein said means for generating a minimum and a maximum width pulse comprise, respectively, a first and a second one shot circuit both coupled to the output of said particle pulse threshold means to receive said threshold pulses; said means for correlating said pulses comprises an exclusive OR gate having one input coupled to the output of said first one shot and a second input coupled to the output of said second one shot; said means for determining if the end of each said threshold pulse does not occur during said time window includes flip-flop circuitry having a pair of inputs coupled to the outputs of said particle pulse threshold means and said exclusive OR gate; and said flip-flop circuitry is operable to provide a bad pulse signal in response to each of said threshold pulses from said particle pulse threshold means only when said flip-flop circuitry is not receiving from said exclusive OR gate a signal representing said time window.

10. The abnormal pulse detector according to any one of claims 1, 2 or 3, which includes bad pulse signal inhibiting means for inhibiting the generation of a bad pulse signal whenever the particle pulse has a peak amplitude lower than a predetermined value.

* * * * *

UNITED STATES PATENT AND TRADEMARK OFFICE
CERTIFICATE OF CORRECTION

PATENT NO. : 4,412,175

DATED : October 25, 1983

INVENTOR(S) : Frank Maynarez

It is certified that error appears in the above—identified patent and that said Letters Patent is hereby corrected as shown below:

Column 5, line 45, change "and" second occurrence to --are--;
Column 6, line 44, change "tha" to --the--;
Column 9, line 2, change "with" to --width--;
Column 10, line 9, after "time" insert --window--.

Signed and Sealed this

Thirty-first Day of January 1984

[SEAL]

Attest:

Attesting Officer

GERALD J. MOSSINGHOFF

Commissioner of Patents and Trademarks